US00PP18330P3

(12) United States Plant Patent
Kaagman

(10) Patent No.: US PP18,330 P3
(45) Date of Patent: Dec. 18, 2007

(54) ***OSTEOSPERMUM* PLANT NAMED 'OSTE WHITEYTWO'**

(50) Latin Name: *Osteospermum ecklonis Norl.*
Varietal Denomination: Oste Whiteytwo

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/392,333

(22) Filed: Mar. 29, 2006

(65) Prior Publication Data

US 2007/0234457 P1 Oct. 4, 2007

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

UPOV–ROM GTITM, Plant Variety Database, 2006/03, GTI Jouve Retrieval Software, citation for 'Oste Whiteytwo'.*

* cited by examiner

*Primary Examiner*—Kent Bell
*Assistant Examiner*—S. B. McCormick-Ewoldt
(74) *Attorney, Agent, or Firm*—Jondle & Associates, P.C.

(57) ABSTRACT

An *Osteospermum* cultivar particularly distinguished by large, white inflorescences with bright blue eyes, deep green and slightly glossy foliage, free and good basal branching, a medium-sized, upright and bushy plant habit, good rooting characteristics, inflorescences that are induced at higher temperatures, floriferousness, good shipping and transportation characteristics and a continuous flowering response throughout the Summer, is disclosed.

1 Drawing Sheet

Genus and species: *Osteospermum ecklonis* Norl.
Variety denomination: 'Oste Whiteytwo'.

BACKGROUND OF THE NEW PLANT

The present invention comprises a new and distinct cultivar of *Osteospermum,* botanically known as *Osteospermum ecklonis* Norl., and hereinafter referred to by the cultivar name 'Oste Whiteytwo'. The new cultivar originated from a hybridization made in the Summer of 2002 in Andijk, The Netherlands. The female parent was the proprietary 'OY-8-10' (unpatented) *Osteospermum* plant, having white inflorescences with blue eyes, while the male parent was the proprietary 'OY-79-2' (unpatented) *Osteospermum* plant, having white inflorescences with blue eyes.

The new cultivar was created in 2002 in Andijk, The Netherlands, and has been asexually reproduced repeatedly by vegetative cuttings and tissue culture in Andijk, The Netherlands, Gilroy, Calif. and Hillscheid, Germany over a three-year period. The present invention has been found to retain its distinctive characteristics through successive asexual propagations.

Plant Breeder's Rights for this cultivar have been applied for in Canada on Mar. 31, 2005 and with the European Union on Dec. 20, 2004.

SUMMARY OF THE INVENTION

The following are the most outstanding and distinguishing characteristics of the new cultivar when grown under normal horticultural practices in Andijk, The Netherlands and Hillscheid, Germany.

1. Large white inflorescences with bright blue eyes;
2. Deep green and slightly glossy foliage;

3. Free-branching with good basal branching;
4. A medium-sized, bushy and upright plant habit;
5. Good rooting characteristics;
6. A continuous flowering response throughout the Summer (in contrast to older varieties which do not flower in the mid-Summer)
7. Inflorescences are induced at higher temperatures (so that an initial cool cultivation period is not necessary)
8. Floriferous (due to good branching and the formation of inflorescences in the Summer); and
9. A good plant for shipping and transportation because the flowers remain open.

DESCRIPTION OF THE PHOTOGRAPH

This new *Osteospermum* plant is illustrated by the accompanying photograph which shows overall plant habit including inflorescences, buds, and foliage of the plant; the colors shown are as true as can be reasonably obtained by conventional photographic procedures.

The photo is of an 11-week-old plant grown in a 12-cm pot in a greenhouse in mid- to late May 2005.

DESCRIPTION OF THE NEW CULTIVAR

The following detailed descriptions set forth the distinctive characteristics of 'Oste Whiteytwo'. The data which define these characteristics were collected from asexual reproductions carried out in Hillscheid, Germany. The plant history was taken on 10-week-old, un-pinched plants grown in 12-cm pots in a greenhouse during late Summer. The color readings were determined under natural light in mid-May from flowers grown in a greenhouse. Color references are to The R.H.S. Colour Chart of The Royal Horticultural Society of London (R.H.S.) (2001).

DESCRIPTION OF THE NEW PLANT

Classification:

*Family.*—Asteraceae.

*Botanical name.*—*Osteospermum ecklonis* Norl.

*Common name.*—African daisy.

Parentage:

*Female parent.*—The proprietary 'OY-8-10' (unpatented) *Osteospermum* plant having white inflorescences with blue eyes.

*Male parent.*—The proprietary 'OY-79-2' (unpatented) *Osteospermum* plant having white inflorescences with blue eyes.

Plant:

*Form and habit.*—Herbaceous perennial but usually cultivated as an annual.

*Growth and branching habit.*—Medium-sized for an *Osteospermum* and freely branching.

*Height* (*from top of soil*).—35 cm to the top of the foliage canopy and 38 cm to the top of the inflorescences.

*Width* (*including inflorescences*).—22 cm.

*Time to produce a finished flowering plant.*—12 to 14 weeks for a 12-cm pot in the Spring.

*Outdoor plant performance.*—Use as bedding plants or in mixed-container plantings.

*Time to initiate and develop roots.*—24–26 days in late Winter.

*Root description.*—Fibrous, fine and freely branching.

Leaves:

*Arrangement.*—Simple and alternate.

*Shape.*—Roughly elliptical to trullate.

*Apex.*—Broadly acute.

*Base.*—Attenuate.

*Margin.*—Entire but the lateral margins are dentate with pointed lobes.

*Texture.*—Upper surface appears to be glabrous, leathery and slightly glossy.

*Immature leaf.*—Color: Upper surface: RHS 143A. Lower surface: RHS 143B.

*Mature leaf.*—Color: Upper surface: RHS 137A to RHS 137B. Lower surface: RHS 137C. Length: 5.5 cm to 6.5 cm. Width: 2.8 cm to 3.2 cm.

*Petioles.*—Length: 0.8 cm to 1.5 cm. Diameter: 0.4 cm. Color: RHS 145A (the midrib and for both the upper and lower surfaces). Texture: Short pubescence along the edge.

Stems:

*Total number of branches.*—8 to 10.

*Length.*—28 cm to 32 cm.

*Diameter.*—0.4 cm to 0.5 cm.

*Internode length.*—1.0 cm to 1.5 cm.

*Color.*—RHS 143C.

*Texture.*—Glabrous.

Inflorescence buds:

*Shape.*—Initially round or onion-shaped; elongate with the development of the ray florets.

*Diameter* (*horizontal*).—0.8 cm to 1.0 cm.

*Height.*—1.8 cm.

*Color* (*at tight bud just before the ray florets unfold*).—RHS 157C.

Inflorescence:

*Type.*—A capitulum or composite-type; solitary inflorescences are borne terminally above the foliage and are radially symmetrical.

*Blooming habit.*—Continuously flowers from Spring through Fall.

*Quantity of inflorescences per plant.*—15 to 20.

*Lastingness of the inflorescences on the plant.*—11 to 14 days.

*Fragrance.*—The inflorescences have a mild fragrance while the leaves have a sharp and spicy fragrance.

*Inflorescence diameter.*—7.2 cm.

*Disc diameter.*—1.2 cm to 1.3 cm.

Disc floret:

*Quantity per inflorescence.*—40 to 50.

*Shape.*—Tube-shaped, while the upper end is 5-lobed, opens outward and is star-shaped.

*Tube color* (*closed*).—RHS 96B (deep blue).

*Tube color* (*mature*).—RHS N81B (violet).

*Length.*—0.8 cm.

*Diameter* (*at apex*).—0.2 cm to 0.3 cm.

*Apex.*—Acute, pointed lobes.

*Apex color.*—RHS N96C (violet-blue).

*Base.*—Fused.

*Margin.*—Entire.

Ray floret:

*Quantity per inflorescence.*—20.

*Shape.*—Ensiform.

*Color.*—Upper surface: Pure white, whiter than RHS 155D; RHS N78B (violet-purple) at the base (near the disc florets). Lower surface: RHS 187C (greyish) alternating, longitudinal stripes; RHS N77D (light grey-purple) and RHS 155D (white) at the margins.

*Length.*—3.8 cm.

*Width.*—Up to 1.0 cm.

*Apex.*—Rounded, slightly retuse.

*Base.*—Fused, narrow tube-shaped.

*Margin.*—Entire.

*Texture.*—Glabrous with very shallow furrows lengthwise; white hair (pappus) at the base.

*Peduncle.*—Length: 3.0 cm to 5.0 cm. Diameter: 0.2 cm to 0.3 cm. Texture: Short pubescence. Color: RHS 143C (light-green).

Phyllaries:

*Arrangement.*—In a whorl, adhere to the lower part of the ray florets.

*Observed quantity per plant.*—15 to 18, with an average number of 15.

*Shape.*—Lanceolate.

*Color.*—Upper (visible) surface: RHS 137D (green). Lower surface: RHS 137D (green).

*Length.*—0.6 cm to 1.2 cm.

*Width.*—0.1 cm to 0.3 cm.

*Apex.*—Acute.

*Base.*—Fused.

*Margin.*—Entire.

*Texture.*—Pubescent (covered with rough hair).

Reproductive organs:

*Androecium.*—Location: Present on disc florets only. Stamen quantity: One per floret. Stamen shape: Tube-shaped. Stamen color: RHS N78C. Stamen length: 0.3 cm to 0.4 cm. Pollen color: RHS 24A (orange). Pollen amount: Abundant.

*Gynoecium.*—Location: Present on ray florets only. Number: One per floret. Pistil length: 0.6 cm. Stigma color: RHS 200A (dark brown). Stigma shape: 2 lobes. Style color: RHS 200A (dark brown). Style length: 0.3 cm to 0.4 cm. Style shape: Filiform (filament-like) with the lobes of the stigma forked and slanting upright (about Y-shaped).

Fruit and seed set: Seed set observed.

*Seed length.*—0.5 cm to 1.0 cm.

*Seed width.*—0.2 cm to 0.3 cm.

*Seed color.*—Golden-brown to black.

*Average amount.*—10 to 20 seeds.

*Fruit development.*—None.

Disease and insect resistance: Average/typical of the species; no special observations made.

COMPARISON WITH PARENTAL AND COMMERCIAL CULTIVARS

'Oste Whiteytwo' differs from the female parent 'OY-8-10' (unpatented) in that the inflorescences of 'Oste Whiteytwo' are smaller with shorter peduncles and has a later flowering response than 'OY-8-10'.

'Oste Whiteytwo' differs from the male parent 'OY-79-2' (unpatented) in that 'Oste Whiteytwo' has a more compact plant habit, better branching and a more vigorous growth habit than 'OY-79-2'.

'Oste Whiteytwo' differs from commercial cultivar 'Brightside' (U.S. Plant Pat. No. 10,596) in that 'Oste Whiteytwo' has brighter blue disc florets, broader leaves, a less distinct anthocyanin coloration of the stems and a more compact plant habit than 'Brightside'.

'Oste Whiteytwo' differs from the commercial cultivar 'Kalanga White' (patent status unknown) in that 'Oste Whiteytwo' has brighter blue disc florets, while 'Kalanga White' has violet disc florets. Additionally, 'Oste Whiteytwo' has wider ray florets, shorter stems and a tighter and more compact plant habit than 'Kalanga White'.

I claim:

1. A new and distinct cultivar of *Osteospermum* plant as shown and described herein.

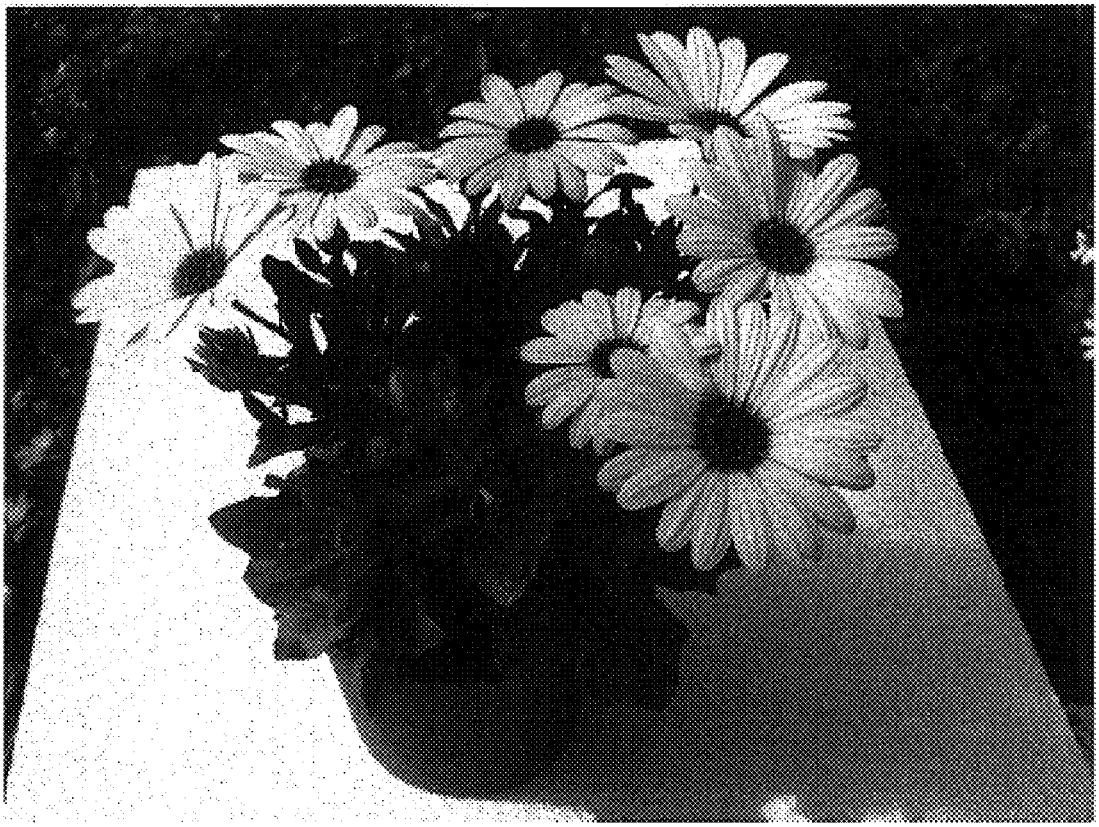

* * * * *